(12) United States Patent
Kodali

(10) Patent No.: US 6,713,117 B1
(45) Date of Patent: Mar. 30, 2004

(54) VEGETABLE OIL HAVING ELEVATED STEARIC ACID CONTENT

(76) Inventor: Dharma Kodali, 710 Olive La. North, Plymouth, MN (US) 55447

( * ) Notice: Subject to any disclaimer, the term of this patent is extended or adjusted under 35 U.S.C. 154(b) by 0 days.

(21) Appl. No.: 09/806,205

(22) PCT Filed: Oct. 1, 1999

(86) PCT No.: PCT/US99/23060
§ 371 (c)(1),
(2), (4) Date: Mar. 27, 2001

(87) PCT Pub. No.: WO00/19832
PCT Pub. Date: Apr. 13, 2000

Related U.S. Application Data

(60) Provisional application No. 60/102,903, filed on Oct. 2, 1998.

(51) Int. Cl.[7] .............................. A23D 9/00; C11B 1/04
(52) U.S. Cl. .......................................... 426/601; 554/9
(58) Field of Search .............................. 426/601; 554/9

(56) References Cited

U.S. PATENT DOCUMENTS

| | | | | |
|---|---|---|---|---|
| 4,910,037 A | * | 3/1990 | Sagi et al. | 426/601 |
| 4,987,071 A | | 1/1991 | Cech et al. | |
| 5,069,915 A | * | 12/1991 | Devitt et al. | 426/93 |
| 5,254,678 A | | 10/1993 | Haseloff et al. | |
| 5,283,124 A | | 2/1994 | Fujibayashi et al. | |
| 5,344,771 A | | 9/1994 | Davies et al. | |
| 5,356,799 A | | 10/1994 | Fabijanski et al. | |
| 5,443,974 A | | 8/1995 | Hitz et al. | |
| 5,451,514 A | | 9/1995 | Boudet et al. | |
| 5,453,566 A | | 9/1995 | Shewmaker et al. | |
| 5,500,361 A | | 3/1996 | Kinney | |
| 5,530,186 A | | 6/1996 | Hitz et al. | |
| 5,530,192 A | | 6/1996 | Murase et al. | |
| 5,532,021 A | * | 7/1996 | Kida et al. | 426/607 |
| 5,668,299 A | | 9/1997 | Debonte et al. | |
| 5,714,668 A | * | 2/1998 | Fehr et al. | 800/312 |
| 5,723,595 A | | 3/1998 | Thompson et al. | |
| 5,767,338 A | | 6/1998 | Fan | |
| 5,795,969 A | | 8/1998 | Fehr et al. | |
| 5,885,643 A | | 3/1999 | Kodali et al. | |
| 6,084,164 A | * | 7/2000 | Bidney et al. | 800/322 |
| 6,229,033 B1 | | 5/2001 | Knowlton | |
| 6,337,100 B1 | * | 1/2002 | Bidney et al. | 426/601 |
| 6,365,802 B2 | * | 4/2002 | Kridl | 800/312 |
| 6,380,462 B1 | * | 4/2002 | Kridl | 800/281 |
| 6,426,448 B1 | * | 7/2002 | Booth et al. | 800/312 |
| 2001/0002489 A1 | * | 5/2001 | Kridl | |

FOREIGN PATENT DOCUMENTS

| | | |
|---|---|---|
| EP | 0 262 113 | 3/1988 |
| EP | 0 323 751 | 7/1989 |
| WO | WO 93/11245 | 6/1993 |
| WO | WO 94/11516 | 5/1994 |
| WO | WO 95/04123 | 2/1995 |
| WO | WO 95/26391 | 10/1995 |
| WO | WO 97/12047 | 4/1997 |
| WO | WO 97/40698 | 11/1997 |
| WO | WO 98/56239 | 12/1998 |

OTHER PUBLICATIONS

Swern, D. 1979. Bailey's Industrial Oil and Fat Products, vol. 1. John Wiley & Sons. New York, p 323.*
Jeyarani, T. 1999, JAOCS 76(12) 1431.*
Gunstone, F. D. 1965. JAOCS 42(11) 961.*
Gunstone, F. D. 1986. The Lipid Handbook. Chapman and Hall, New York, p. 98–100.*
U.S. PVP Certificate No. 9100151.
Bailey's Industrial Oil & Fat Products, 5th Edition, 1996, vol. 4, John Wiley & Sons, Inc., pp. 382–390, 403.
de Feyter and Gaudron, "Expressing Ribozymes in Plants," *Meth. Mol. Biol*, 1997, Chapter 43, vol. 74, pp. 403–415.
Kaestner et al., "Differentiation–induced Gene Expression in 3T3–L1 Preadipocytes," *J. Biol. Chem.*, 1989, 264(25):14755–14761.
Lees, "Gums and Pastilles—Gum Acacia—Melting—Sieving—Gelatine—Soaking—Depositors—Condition of the Moulding Starch—Stoving—Cleaning and Finishing—Sugar Sanding," *A Course in Confectionary*, 2nd Edition, 1980, Specialised Publications Ltd., Surrey, United Kingdom, pp. 98–106.
Minifie, "History of Coca and Chocolate," *Chocolate, Cocoa and Confectionery*, 3rd Edition, 1989, Van Nostrand Reinhold, New York, pp. 1–27.
Murphy and Cummins, "Biosynthesis of Seed Storage Products during Embryogenesis in Rapeseed, Brassica napus," *J. Plant Physiol.*, 1989, 135:63–69.
Pleines and Friedt, "Breeding for Improved C18–Fatty Acid Composition in Rapeseed (*Brassica napus* L.)," *Fat Sci. Technol.*, 1988, 90:167–171.
Perriman et al., "Effective ribozyme delivery in plant cells," *Proc. Natl. Acad. Sci. USA*, 1995, 92:6175–6179.
Rakow and McGregor, "Opportunities and Problems in Modifications of Levels of Rapeseed $C_{18}$ Unsaturated Fatty Acids," *J. Am. Oil Chem. Soc.*, 1973, 50(7):400–403.
Roy and Tarr, "Prospects for the Development of Rapeseed (*B. napus* L.) with Improved Linoleic and Linolenic Acid Content," *Plant Breeding*, 1987, 98:89–96.
Roy and Tarr, "IXLIN—an Interspecific Source for High Linoleic and Low Linolenic Acid Content in Rapeseed (*Brassica napus* L.)," *Z. Pflanzenzüchtg.*, 1985, 95:201–209.
Scarth et al., "Stellar Low Linolenic–High Linoleic Acid Summer Rape," *Can. J. Plant Sci.*, 1988, 68:509–511.

(List continued on next page.)

Primary Examiner—Carolyn Paden
(74) Attorney, Agent, or Firm—Fish & Richardson P.C., P.A.

(57) ABSTRACT

Vegetable oils having an elevated stearic acid content and a low polyunsaturates content are described. A confectionery product containing oils of the invention is also described.

40 Claims, 2 Drawing Sheets

OTHER PUBLICATIONS

Scheffler et al., "Desaturase multigene families of *Brassica napus* arose through genome duplication," *Theor. Appl. Genet.*, 1997, 94:583–591.

Stukey et al., "The OLE1 Gene of *Saccharomyces cerevisiae* Encodes the Δ9 Fatty Acid Desaturase and Can Be Functionally Replaced by the Rat Stearoyl–CoA Desaturase Gene," *J. Biol. Chem.*, 1990, 265(33):20144–20149.

Swern (ed.), *Bailey's Industrial Oil and Fat Products*, vol. 1, Fourth Edition, 1979, John Wiley & Sons, New York, pp. 322–325.

Thiede et al., "Construction and Sequence of cDNA for Rat Liver Stearyl Coenzyme A Desaturase," *J. Biol. Chem.*, 1986, 261(28):13230–13235.

* cited by examiner

VEGETABLE OIL HAVING ELEVATED STEARIC ACID CONTENT

CROSS REFERENCE TO RELATED APPLICATIONS

This application is a 35 U.S.C. §371 application of US99/23060, which claims priority from U.S. Ser. No. 60/102,903, filed Oct. 2, 1998.

TECHNICAL FIELD

This invention relates to vegetable oils that contain an altered fatty acid content, more particularly, an elevated stearic acid content and a decreased polyunsaturates content.

BACKGROUND OF THE INVENTION

Cocoa butter is dominated by three fatty acids, palmitic, stearic and oleic acid, and three triacylglycerols (TAGs) containing these particular fatty-acids. Approximately 80% of the TAGs within cocoa butter are palmitate-oleate-palmitate (13–19%), palmitate-oleate-stearate (36–42%), and stearate-oleate-stearate (23–29%). Since cocoa butter is expensive, and its supply is limited, various alternatives have been proposed. Cocoa butter replacers are typically derived from partially hydrogenated, or partially hydrogenated and fractionated blends of soybean, canola, and palm oils. As such, these oils have a high amount of trans fatty acids. See, for example, *Bailey's Industrial Oil & Food Products*, Fifth Edition, John Wiley & Sons, Inc., Vol. 4, pp. 384–389 (1996).

Cocoa butter substitutes generally contain lauric acid as a main component (40–50%), and are typically derived from the oil and coconut palm. Genetic engineering has led to other plant sources having elevated levels of lauric acid. For example, U.S. Pat. No. 5,344,771 describes transgenic Brassica plants that produce canola oil that is rich in lauric acid.

Cocoa butter equivalents and extenders have a TAG composition that is similar to cocoa butter. Cocoa butter equivalents are derived from palm, illipe, shea, sal and kokum fats. Attempts to create other cocoa butter equivalents from oilseed plants have not been successful. For example, U.S. Pat. No. 5,723,595 describes transgenic Brassica plants that contain a delta-9 desaturase transgene. Oils extracted from these plants have increased amounts of stearic acid, but also contain increased amounts of linolenic acid and/or increased levels of long chain and very long chain fatty acids (18 carbons or greater).

Brassica plant lines with reduced levels of linolenic acid (2.5–5.8%) and elevated levels of oleic acid (73–79%) have been described (Pleines et al., *Fat Sci. Technol.,* 90:167–171, 1988). Although there are certain problems associated with selecting mutant plants that have an altered content of linoleic and linolenic acids (Rakow et al., *J. Amer. Oil Chem. Soc.,* 50:400–403, 1973), Stellar summer rapeseed oil that contains 3% linolenic acid and 28% linoleic acid has been reported (*Can. J. Plant Sci.,* 68:509–511, 1988). In addition, a reconstituted line characterized by low linolenic and high linoleic content was produced by gene transfer in an interspecies cross from *Brassica juncea* into *Brassica napus* (Roy et al., *Z. Pflanzenzuchtg,* 95:201–209, 1985). Prospects for the development of *Brassica napus* having improved linolenic and linoleic acid content also have been reported (Roy et al., *Plant Breeding,* 98:89–96, 1987). Seeds and oils having 79% oleic acid and 3.5% α-linolenic acid also have been reported (European Patent application 323 751).

SUMMARY OF THE INVENTION

The invention features vegetable oils that have an elevated stearic acid content and a decreased polyunsaturated fatty acid content when compared with known vegetable oils.

In one aspect, the invention features an endogenous oil extracted from plant seeds that has a stearic acid content of about 15% to about 30% (e.g., 17% to about 28%) and a polyunsaturated fatty acid content of about 2% to about 15% (e.g., about 2% to about 6%). The oil can have an α-linolenic acid content of about 0.6% to about 2.0% and/or a palmitic acid content of about 6% to about 20%. For example, the oil can have a palmitic acid content of about 7% to about 19%. The oil can have an oleic acid content of less than about 64%, e.g., about 46% to about 53%. The iodine value of such oils is less than about 76. Oils of this embodiment can have a differential scanning calorimetry (DSC) melting point of about 4° C. to about 20° C. in the absence of cold storage crystallization and a DSC melting point of about 24° C. to about 40° C. following cold storage crystallization. The endogenous oil can be extracted from Brassica seeds.

In another aspect, the invention features an oil having a stearic acid content of about 19% to about 30% and a polyunsaturated fatty acid content of about 2% to about 15%. Such an oil further has a palmitic acid content of about 6% to about 19% and/or an oleic acid content of about 46% to about 53%. An oil of this embodiment has a DSC melting point of about 30° C. to about 40° C. in the absence of a cold storage period. About 15% or more of the TAGs in the oil (e.g., about 18% or more or 30% or more) include an oleate moiety at the sn-2 position and palmitate or stearate moieties at the sn-1 and sn-3 positions. About 10% to about 25% of the TAGs in the oil can have a stearate moiety at the sn-1 position, an oleate moiety at the sn-2 position, and a stearate moiety at the sn-3 position; and about 6% to about 12% of TAGs in the oil can have a palmitate moiety at the sn-1 position, an oleate moiety at the sn-2 position, and a stearate moiety at the sn-3 position.

The invention also features a vegetable oil, wherein at least about 15% of the TAGs in the oil include an oleate moiety at the sn-2 position and palmitate or stearate moieties at the sn-1 and sn-3 positions. For example, at least about 18% or at least about 30% of the TAGs can include an oleate moiety at the sn-2 position and palmitate or stearate moieties at the sn-1 and sn-3 positions.

In another aspect, the invention features a method of producing a vegetable oil. The method includes crushing seeds produced by a plant (e.g., a Brassica plant), wherein the seeds have a stearic acid content of about 15% to about 30% and a polyunsaturated fatty acid content of about 2% to about 15%; and extracting an endogenous oil from the crushed seeds. The Brassica plant can exhibit reduced delta-9 desaturase activity and reduced delta-12 desaturase activity, and increased stearoyl acyl-ACP thioesterase activity. The Brassica plant further can exhibit a reduced delta-15 desaturase activity. The endogenous oil can have a palmitic acid content of about 6% to about 20%. The method further can include the step of fractionating the endogenous oil into a stearine fraction and an olein fraction, wherein the stearine fraction has a stearic acid content of about 20% to about 30% and an oleic acid content of about 46% to about 53%.

In a further aspect, the invention features a confectionery product that includes a fat component, wherein the fat component includes a vegetable oil having a stearic acid content of about 20% to about 30% and a polyunsaturated fatty acid content of about 2% to about 15%. The vegetable oil further can have an oleic acid content of about 46% to about 53%. The invention also features a confectionery product that includes a fat component, wherein at least about 18% of the TAGs in the fat component include an oleate moiety at the sn-2 position and palmitate or stearate moieties at the sn-1 and sn-3 positions. The fat component can be derived from canola, soy, corn, or sunflower.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DETAILED DESCRIPTION

Figure 1:
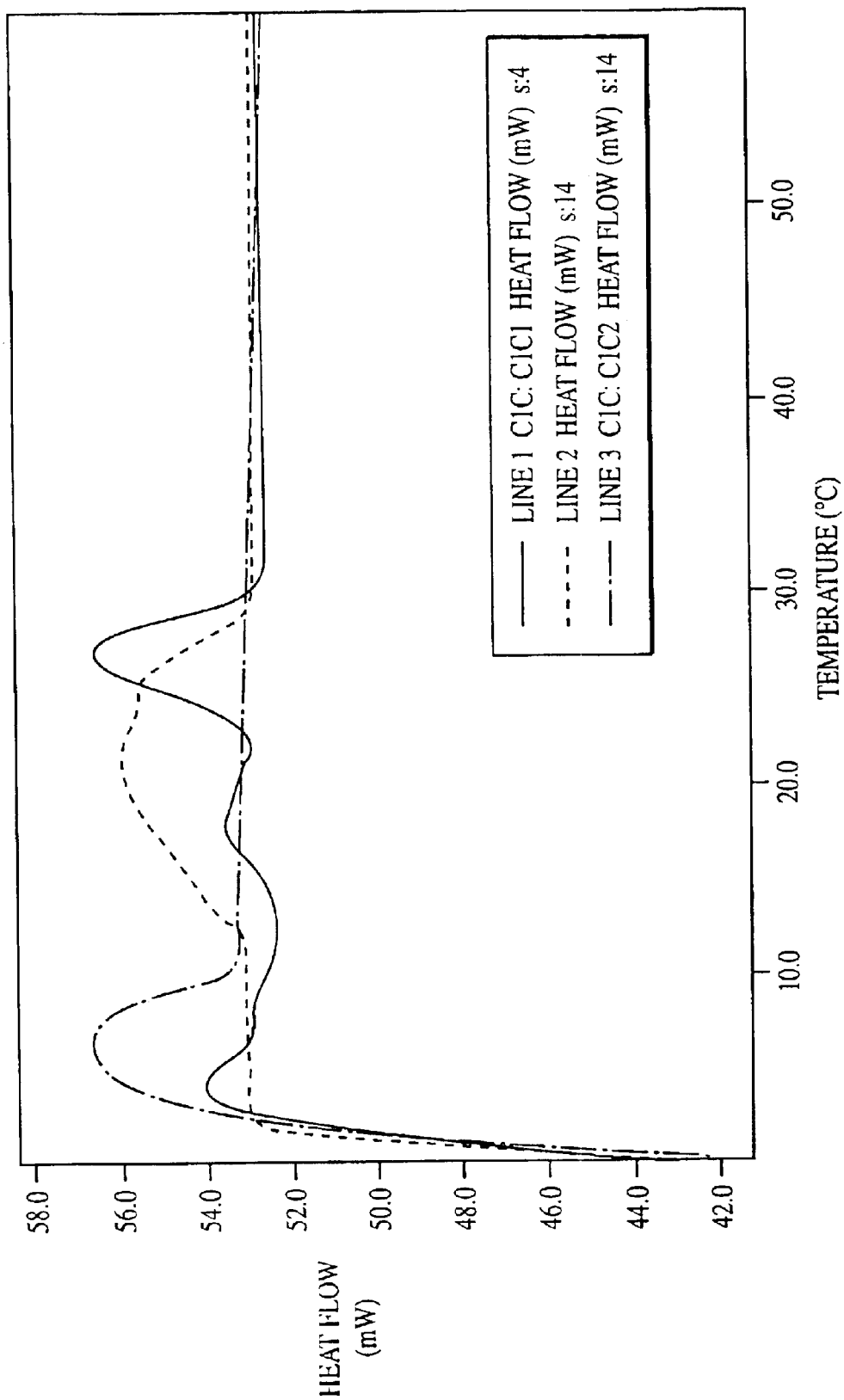
FIG. 1 is a DSC scan of C1C oil after tempering at 10° C. for 1 or 15 hours. Line 1 is a melting curve for C1C oil that was incubated at 5° C. for 1 month. Line 2 is a melting curve for C1C oil that was completely melted, cooled to 10° C., and held at 10° C. for 15 hours. Line 3 is a melting curve for C1C oil that was completely melted, cooled to 10° C., and held for 1 hour.

The invention features vegetable oils that have an elevated stearic acid content and a decreased polyunsaturated fatty acid content when compared with known vegetable oils. The stearic acid content is sufficiently elevated to allow the oils to be used in foods that require solid fats, such as spreads and shortenings, without the need for hydrogenation. As such, oils of the invention are nutritional, natural compositions that contain no trans fatty acids and have high oxidative stability. Moreover, formulation of the high stearic oils of the invention with various base stocks can provide the means to create numerous solid fat applications.

Plants Containing Elevated Stearic Acid and Decreased Polyunsaturated Fatty Acids It has been discovered that plants can be manipulated to produce high levels of stearate and low levels of polyunsaturated fatty acids through genetic engineering, mutagenesis or combinations thereof, and that vegetable oils having a stearic acid content of about 15% to about 30% and a polyunsaturated fatty acid content of about 2% to about 15%, based on total fatty acid composition, can be obtained from crushing seeds of such plants and extracting the oil therefrom.

Plant species that are suitable for producing oils of the invention include Brassica spp. (canola-type rapeseed), *Glycine max* (soybean), Helianthus (sunflower) and *Zea mays* (corn). For example, Brassica species such as *B. napus, B. campestris, B. juncea,* and *B. rapa*, are suitable for producing the oils of the invention. In general, the levels of oleic acid and polyunsaturated fatty acids are decreased in the modified plants in comparison with the starting plant, in order to increase the saturated fatty acid content, and in particular, the stearic acid content. Brassica plants can be modified such that they contain increased oleoyl- or stearoyl-ACP thioesterase activity and decreased fatty acid desaturase activities, including delta-9, delta-12, and delta-15 desaturase activities. Plants also can be modified such that they contain increased 3-ketoacyl-ACP synthase II (KAS II). Increased thioesterase activity may not be necessary if delta-9 desaturase activity is completely inhibited. Brassica plants also can exhibit increased palmitoyl-ACP thioesterase activity.

The genome of many Brassica species is complex. For example, *B. juncea* and *B. napus* are amphidiploid or allotetraploid, and have a complete diploid chromosome set from each parent. It is estimated that *B. napus* contains six copies of the microsomal delta-15 desaturase and eight copies of the corresponding plastid desaturase. Scheffler, J. A. et al., *Theor. Appl. Genet.*, 94:583–591 (1997). "Microsomal desaturase" refers to the cytoplasmic location of an enzyme, while "plastid desaturase" refer to the plastid location of the enzyme. These fatty acid desaturases have not been isolated and characterized as proteins.

Plants such as soybean, sunflower, and corn will exhibit an elevated stearic acid content and a reduced polyunsaturates content in the seed oil when appropriately modified. For example, generic soybean oil contains high levels of linoleic acid (about 50%). Polyunsaturates can be reduced in soybean by decreasing delta-12 desaturase activity. Such soybean plants have an elevated oleic acid content. See, for example, WO 97/40698. Stearic acid can be increased in high oleic acid soybean lines, for example, by increasing acyl-ACP thioesterase activity and/or reducing delta-9 desaturase activity. Similar modifications can be made in sunflower and corn plants.

A plant described herein may be used as a parent to develop a plant line, or may itself be a member of a plant line, i.e., it is one of a group of plants that display little or no genetic variation between individuals for the novel oil composition trait. Such lines can be created by several generations of self-pollination and selection, or vegetative propagation from a single parent using tissue or cell culture techniques known in the art. Additional means of breeding plant lines from a parent plant are known in the art.

Transgenic plants can be obtained by introducing at least one nucleic acid construct into a plant cell as described herein. Seeds produced by a transgenic plant can be grown and selfed (or outcrossed and selfed) to obtain plants homozygous for the construct. Seeds can be analyzed to identify those homozygotes having the desired expression of the construct. Transgenic plants can be entered into a breeding program, e.g., to increase seed, to introgress the novel construct into other lines or species, or for further selection of other desirable traits. Alternatively, transgenic plants can be obtained by vegetative propagation of a transformed plant cell, for those species amenable to such techniques.

Progeny of a transgenic plant are included within the scope of the invention, provided that such progeny exhibit the novel seed oil characteristics disclosed herein. Progeny of an instant plant include, for example, seeds formed on $F_1$, $F_2$, $F_3$, and subsequent generation plants, or seeds formed on $BC_1$, $BC_2$, $BC_3$, and subsequent generation plants.

Transgenic techniques for use in the invention include, without limitation, Agrobacterium-mediated transformation, electroporation, and particle gun transformation. Illustrative examples of transformation techniques are described in WO 99/43202 and U.S. Pat. No. 5,204,253 (particle gun) and U.S. Pat. No. 5,188,958 (Agrobacterium). Transformation methods utilizing the Ti and Ri plasmids of Agrobacterium spp. typically use binary type vectors. Walkerpeach, C. et al., in Plant Molecular Biology Manual, S. Gelvin and R. Schilperoort, eds., Kluwer Dordrecht, C1:1–19 (1994). If cell or tissue cultures are used as the recipient tissue for transformation, plants can be regenerated from transformed cultures by techniques known to those skilled in the art. In addition, various plant species can be transformed using the pollen tube pathway technique.

Plants useful in the invention exhibit an increase in stearic acid content in seeds produced by such plants, in comparison with a corresponding non-transgenic plant. Such an increase typically is due to an elevated thioesterase activity towards stearoyl-ACP. Acyl-ACP thioesterases that utilize stearoyl-ACP as a substrate include oleoyl-ACP thioesterases and stearoyl-ACP thioesterases. Such thioesterases hydrolyze stearoyl-ACP into free stearate and ACP. Nucleic acids encoding such thioesterase sequences are described, for example, in WO 97/12047 and U.S. Pat. No. 5,530,186. The activity of such thioesterases can be increased in a plant by operably linking a thioesterase coding sequence to one or more regulatory elements in sense orientation and introducing the construct into a plant cell using techniques and regulatory sequences as described herein. The additional gene dose results in more thioesterase gene product and increased enzyme activity.

Plants useful in the invention also exhibit a reduced polyunsaturates content in seeds. Such plants can be created by causing a reduction in the activity of appropriate fatty acid desaturases. By "fatty acid desaturase" is meant an enzyme that catalyzes the breakage of a carbon-hydrogen bond and the formation of a carbon-carbon double bond into a fatty acid molecule. The fatty acid may be free or esterified to another molecule including, but not limited to, acyl-carrier protein (ACP), coenzyme A, sterols, and the glycerol moiety of glycerolipids. For example, the enzyme delta-12 fatty acid desaturase (also known as oleic desaturase, omega-6 fatty acid desaturase, and cytoplasmic oleic desaturase) is involved in the enzymatic conversion of oleic acid to linoleic acid. Delta-12 desaturase catalyzes the formation of a double bond between carbon atoms at positions 6 and 7 of an 18 carbon-long fatty acyl chain, numbered from the methyl end. These same carbon atoms may be referred to as residing at positions 12 and 13 if numbered from the carbonyl carbon. The nucleotide sequences of higher plant genes encoding microsomal delta-12 fatty acid desaturase are described in Lightner et al., WO94/11516. The gene encoding delta-12 fatty acid desaturase is referred to as fad2 in Brassica and Arabidopsis. A reduction in delta-12 desaturase activity can be achieved by techniques including, but not limited to, antisense, ribozyme cleavage, dominant negative suppression and co-suppression. These phenomena can significantly reduce expression of the gene product of the native gene. A reduction in fad2 gene expression and delta-12 desaturase activity can be inferred from the decreased level of reaction product (e.g., decreased 18:2) and the increased level of substrate in seeds compared with the corresponding levels in non-transgenic plants.

Delta-9 desaturase catalyzes the desaturation of stearoyl-ACP (18:0) at the $\Delta 9$ position, to yield oleoyl-ACP (18:1) and is often referred to as a "stearoyl-ACP desaturase" because of its high activity toward stearate. Nucleotide sequences encoding microsomal delta-9 desaturases from yeast, rat, and mice have been described. Stukey, et al., *J. Biol. Chem.*, 265:20144–20149, (1990); Thiede et al., *J. Biol. Chem.*, 261:13230–13235, (1986); Kaestner et al., *J. Biol. Chem.*, 264:14755–14761, (1989). Nucleotide sequences encoding delta-9 desaturases from higher plants also have been described. See, for example, U.S. Pat. Nos. 5,443,974 and 5,723,595. A reduction in delta-9 desaturase activity can be achieved by such techniques as antisense, ribozyme cleavage, dominant negative suppression and co-suppression.

Plants useful in the invention also can exhibit a reduction in delta-15 fatty acid desaturase activity in comparison with a corresponding non-transgenic plant. Delta-15 fatty acid desaturase (also known as omega-3 fatty acid desaturase, cytoplasmic linoleic acid desaturase, and linoleate desaturase) is involved in the enzymatic conversion of linoleic acid to α-linolenic acid. Delta-15 desaturase catalyzes the formation of a double bond between carbon atoms residing at positions 3 and 4 (numbered from the methyl end of the molecule) of an 18 carbon-long fatty acyl chain. These same carbon atoms may be referred to as residing at positions 15 and 16 when counted from the carbonyl carbon. The gene encoding delta-15 fatty acid desaturase is referred to as fad3 in Brassica and Arabidopsis. Sequences of higher plant genes encoding microsomal and plastid fad3 desaturases are disclosed, for example, in WO 93/11245. A reduction in delta-15 desaturase activity can be achieved by techniques including, but not limited to, antisense, ribozyme cleavage, dominant negative suppression and co-suppression.

Increased expression of KAS II, which elongates palmitoyl-ACP to stearoyl-ACP, can be used to increase stearoyl-ACP levels. Plant KAS II sequences are described, for example, in U.S. Pat. No. 5,500,361. Plants can be produced that overexpress KAS II in combination with decreased desaturase activity and/or increased thioesterase activity.

Suitable nucleic acid constructs for modifying expression of thioesterases, desaturases, or KAS II, include a regulatory sequence operably linked to the desired coding sequence. Regulatory sequences typically do not themselves code for a gene product. Instead, regulatory sequences affect the expression of the coding sequence. Examples of regulatory sequences are known in the art and include, without limitation, promoters of genes expressed during embryogenesis, e.g., a napin promoter, a phaseolin promoter, an oleosin promoter, a cruciferin promoter and constitutive promoters such as the cauliflower mosaic virus 35S promoter. Native regulatory sequences, including the native promoters of delta-9, delta-12, and delta-15 fatty acid desaturase genes, KAS II, and oleoyl- and stearoyl-ACP thioesterase genes also can be used in constructs of the invention. Other examples of suitable regulatory sequences include enhancers or enhancer-like elements, introns, and 5' and 3' untranslated sequences. Further examples of suitable regulatory sequences for the proper expression of delta-9, delta-12 or delta-15 desaturases, KAS II, and acyl-ACP thioesterase coding sequences are known in the art.

In preferred embodiments, regulatory sequences are seed-specific, i.e., the particular gene product is preferentially expressed in developing seeds and expressed at low levels or not at all in the remaining tissues of the plant. Seed-specific regulatory sequences preferably stimulate or induce expression of the recombinant desaturase coding sequence fragment at a time that coincides with or slightly precedes expression of the native desaturase or thioesterase gene. Murphy et al., *J. Plant Physiol.* 135:63–69 (1989).

Typically, nucleic acid molecules encoding thioesterases, desaturases, or KAS II are introduced into a parent plant on separate plasmids. However, it is recognized in the art that plasmids or vectors can carry more than one antisense, co-suppression, or overexpression nucleic acid molecule, each of which may be under the control of the same or different regulatory elements.

The preparation of antisense and co-suppression constructs for reducing desaturase activity utilize the transcribed sequence of the desaturase gene or fragments thereof. Antisense RNA has been used to inhibit plant target genes in a tissue-specific manner. See, for example, U.S. Pat. Nos. 5,453,566, 5,356,799, and 5,530,192. Antisense nucleic acid constructs include a partial or a full-length coding sequence operably linked to at least one suitable regulatory sequence in antisense orientation.

Desirable alterations in fatty acid levels in the seed oil of plants can be produced using a ribozyme. Ribozyme molecules designed to cleave delta-9, delta-12 desaturase, or delta-15 desaturase mRNA transcripts can be used to prevent expression of functional delta-9, delta-12, and delta-15 desaturases. While various ribozymes that cleave mRNA at site-specific recognition sequences can be used to destroy desaturase mRNAs, hammerhead ribozymes are particularly useful. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is well known in the art. See, for example, U.S. Pat. No. 5,254,678. Hammerhead ribozyme sequences can be embedded in a stable RNA such as a transfer RNA (tRNA) to increase cleavage efficiency in vivo. Perriman, R. et al., *Proc. Natl. Acad. Sci. USA*, 92(13):6175–6179 (1995); de Feyter, R. and Gaudron, J., *Methods in Molecular Biology*, Vol. 74, Chapter 43, "Expressing Ribozymes in Plants", Edited by Turner, P. C, Humana Press Inc., Totowa, N.J. (1997). RNA endoribonucleases such as the one that occurs naturally in *Tetrahymena thermophila*, and which have been described extensively by Cech and collaborators are also useful. See, for example, U.S. Pat. No. 4,987,071.

The phenomenon of co-suppression also has been used to inhibit plant target genes in a tissue-specific manner. Co-suppression of an endogenous gene using a full-length cDNA sequence as well as a partial cDNA sequence are known. See, for example, WO 94/11516, and U.S. Pat. Nos. 5,451,514 and 5,283,124. Co-suppression of delta-9, delta-12, or delta-15 desaturase activity in plants can be achieved by expressing, in the sense orientation, the entire or partial coding sequence of a desaturase gene.

Mutagenesis can also be used to reduce delta-9, delta-12, or delta-15 desaturase activity in plants. Mutagenic agents can be used to induce random genetic mutations within a population of seeds or regenerable plant tissue. Suitable mutagenic agents include, for example, ethyl methyl sulfonate, methyl N-nitrosoguanidine, ethidium bromide, diepoxybutane, x-rays, UV rays, and other mutagens known in the art. The treated population, or a subsequent generation of that population, is screened for reduced desaturase or enhanced thioesterase activity that results from the mutation. Mutations can be in any portion of a gene, including the coding region, introns, and regulatory elements, that render the resulting gene product non-functional or with reduced activity. Suitable types of mutations include, for example, insertions or deletions of nucleotides, and transitions or transversions in the wild-type coding sequence. Such mutations can lead to deletion or insertion of amino acids, and conservative or non-conservative amino acid substitutions in the corresponding gene product.

Brassica plant lines having mutations in desaturase genes are known. For example, IMC 129 (U.S. PVP Certificate No. 9100151; U.S. Pat. No. 5,668,299) contains a mutation in a delta-12 desaturase gene and produces oil containing about 75.6% oleic acid and about 4.9% α-linolenic acid. *Brassica napus* line IMC 130 carries the delta-12 desaturase mutation of IMC 129 as well as a defect causing a reduced α-linolenic acid content in seeds, presumably due to a mutation in a delta-15 fatty acid desaturase gene. See, U.S. Pat. No. 5,767,338.

Characterization of Oils

Techniques that are routinely practiced in the art can be used to extract, process, and analyze the oils produced by plants of the instant invention. Typically, plant seeds are cooked, pressed, and extracted to produce crude oil, which is then degummed, refined, bleached, and deodorized. Generally, techniques for crushing seed are known in the art. For example, soybean seeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

The majority of the seed oil is released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures (i.e., degumming, caustic refining, bleaching, and deodorization). Degumming can be performed by addition of concentrated phosphoric acid to the crude oil to convert non-hydratable phosphatides to a hydratable form, and to chelate minor metals that are present. Gum is separated from the oil by centrifugation. The oil can be refined by addition of a sufficient amount of a sodium hydroxide solution to titrate all of the fatty acids and removing the soaps thus formed.

Deodorization can be performed by heating the oil to 500° F. (260° C.) under vacuum, and slowly introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. If the amount of oil is limited, the oil can be placed under vacuum, e.g., in a Parr reactor and heated to 500° F. for the same length of time that it would have been deodorized. This treatment improves the color of the oil and removes a majority of the volatile substances.

Oils of the invention are extracted from seeds and have a stearic acid content of about 15% to about 30% and a polyunsaturated fatty acid content of about 2% to about 15%, based on total fatty acid composition. As used herein, "polyunsaturated fatty acid content" refers to the total amount of linoleic acid ($C_{18:2}$) and α-linolenic acid ($C_{18:3}$). In particular, the stearic acid content can be about 17% to about 28%, and the polyunsaturated fatty acid content can be about 2% to about 6%. The α-linolenic acid content can be about 0.6% to about 2.0%. Oils of the invention also can have a palmitic acid content of about 4% to about 20% (e.g. about 6% to about 20%), and in particular, about 7% to about 19%. The oleic acid content of such oils is less than about 64%. For example, the oleic acid content can be about 34% to about 53%, about 34% to about 46%, or about 46% to about 53%. The iodine value of such oils is less than about 76. For example, the iodine value can be about 35 to about 64 or about 60 to about 74. Iodine value is a measure of oil saturation. Oils that have higher iodine values are considered less saturated than oils with lower iodine values.

Oil composition is typically analyzed by extracting fatty acids from bulk seed samples (e.g., at least 10 seeds). Fatty acid TAGs in the seed are hydrolyzed and converted to fatty acid methyl esters. Thus, the percentages of fatty acids set forth herein, unless otherwise designated, are on a weight basis and refer to the percentage of the fatty acid methyl ester in comparison with the total fatty acid methyl esters in the sample being analyzed. Those seeds having an altered fatty acid composition may be identified by techniques known to the skilled artisan, e.g., gas-liquid chromatography (GLC) analysis of a bulked seed sample, a single seed or a single half-seed. Half-seed analysis is well known in the art to be useful because the viability of the embryo is maintained and thus those seeds having what appears to be a desired fatty acid profile may be planted to form the next generation. However, bulk seed analysis typically yields a more accurate representation of the fatty acid profile of a given genotype. Fatty acid composition can also be determined on larger samples, e.g., oil obtained by pilot plant or commercial scale refining, bleaching and deodorizing of endogenous oil in the seeds.

Oils of the invention have a melting point of about 4° C. to about 20° C. in the absence of tempering or cold storage crystallization, e.g., after refining, bleaching, and deodorizing an endogenous oil. Surprisingly, these oils have a melting point of about 24° C. to about 40° C. (e.g., about 24° C. to about 30° C., about 24° C. to about 37° C., or about 30° C. to about 37° C.) following a tempering period or cold storage crystallization. Cold storage crystallization refers to a tempering period in which the oil is maintained at a cool temperature for a period of time sufficient to change the melting profile of the oil. Without being bound to any particular mechanism, it is thought that a tempering period allows the oils to crystallize into a higher melting polymorphic form. Cold storage at temperatures of about 2° C. to about 12° C. for at least about 10 hours is sufficient to increase the melting point. For example, the oil can be maintained at about 2° C. to about 7° C. for 12 hours, 7 days, or about 2 months. Alternatively, the oil can be maintained at about 10° C. for 15 hours. Melting points referred to above are determined by differential scanning calorimetry (DSC) using a Perkin Elmer Model 7 differential scanning calorimeter. It is apparent, however, that melting points can be determined by other techniques, including Mettler Drop Point and visual inspection of material in a capillary tube in a water or oil bath.

Oils of the invention can be fractionated to obtain a solid or stearine fraction having a high stearic acid content and a high melting point. The unfractionated product is fractionally crystallized under controlled conditions, then separated into a solid fraction and a liquid oil fraction by techniques known in the art, e.g., plate and frame filtration, pressure filtration, or centrifugation. Dry fractionation procedures may be used to separate the liquid and solid fractions of oils, e.g., an oil is crystallized at 10° C. for 15 hours and at 16° C. for 24 hours, centrifuged, and the liquid is separated. Alternatively, the fractions from the crystallized mixture are separated by pressure or vacuum filtration. Pressure filtration typically uses an inert gas, e.g., $N_2$ from about 14.7 psi to about 300 psi (101.3 kPa to 2067.9 kPa). See, e.g., EP 262 113, WO95/04123, and WO95/26391. In addition, a combination of the above procedures can be used to separate the liquid and solid fractions.

The fractionation step can be repeated on the stearine obtained from the first fractionation. In this step, the stearine is melted, then re-crystallized under controlled conditions as described above. The stearine fraction obtained from the second fractionation (stearine #2) also has a high stearic acid content and a high melting point. Such oils have a stearic acid content of about 19% to about 30% (e.g. about 20% to about 30%) and a melting point of about 28° C. to about 42° C. The oleic acid content of such oils can be about 46% to about 53%.

A significant proportion of the TAG moieties in oils of the invention are structured such that an oleate moiety (O) is at the sn-2 position and a palmitate (P) or a stearate (S) moiety is at the sn-1 and sn-3 positions ($^P/_S O^P/_S$). Similar nomenclature is used to describe other TAGS. TAGs of the structure $^P/_S O^P/_S$ can compose about 15% of the TAGs in the oil, about 18% to about 30% of the TAGs, or at least about 30% of the TAGs in the oil. In particular, about 31% or more of the TAGs are $^P/_S O^P/_S$. For example, about 10% to about 25% of the TAGs in an oil of the invention are SOS, and about 4% to about 12% (e.g. about 6% to about 12%) of the TAGs in the oil are POS. A further increase in the percentage of TAGs in these particular conformations is desirable for solid fat applications. The proportions of TAGs in oils of the invention can be readily determined according to AOCS Official Method Ce 5B-89. Individual TAGs are identified by comparison with external or internal standards and can be quantified using a non-linear quadratic fit curve.

TAGs such as SOS and POS appear to concentrate in the stearine fractions of oils of the invention, providing the stearine with desirable physical characteristics, including melting profile, saturated fatty acid content, and solid fat content. The olein fractions contain TAGs with higher degrees of unsaturation, such as OOO (triolein) and OOS. Oils of the invention contain little if any trisaturated TAGs (e.g., SSS, SSP, PPP, etc.).

The oils of the invention contain from about 12% to about 43% solid fat at 10° C. (e.g. about 16% to about 43%). The first stearine fraction has a solid fat content of about 20% to about 25% at 10° C. and less than about 1% at 21.1° C. The second stearine fraction has a solid fat content that ranges from about 20% to about 15% at temperatures of about 21° C. to about 27° C., respectively. Solid fat is an indicator of the solid fat present over a defined temperature scale and can be measured by a Solid Fat Index (SFI) or by Solid Fat Content (SFC). SFC is typically measured by pulsed nuclear magnetic resonance (NMR). See, AOCS Official Method Cd 16b-93. SFI is generally measured by dilatometry and utilizes a series of temperature-controlled baths at 10, 21.1, 26.7, 33.3 and 40° C. and glass dilatometers for determining volume of the sample at each temperature. See, *Bailey's Industrial Oil & Food Products*, Fifth Edition, John Wiley & Sons, Inc., Vol. 4, p. 403 (1996).

Oil Compositions

The invention features a product that includes a fat component, wherein the fat component comprises an oil of the invention. As used herein, a "fat component" can be an oil (liquid) or can be a fat (solid or semi-solid). Oils of the invention can be used to replace or extend a fat such as cocoa butter in confectionery products, e.g., chocolate or other food products. Oils of the invention provide particularly useful cocoa butter substitutes, at least in part due to the lower polyunsaturates content and the particular TAG content in comparison with known vegetable oils.

For example, oils of the invention can replace about 1% to about 100% (e.g., about 10% to about 100%) of the cocoa butter in confectionery compositions. Such compositions also can contain, for example, sugars (e.g., sucrose, fructose, glucose, and maltose), water, flavorings such as cocoa powder, chocolate liquor, cocoa mass, vanilla, nut flavorings, and fruit flavorings, or milk solids (non-fat, skimmed, or whole). In addition, the compositions can contain emulsifiers such as lecithin, synthetic phospholipids, and sorbitan esters to either improve rheological properties or crystallization. Antioxidants, dietary fibers, vitamins, bulking or bodying agents such as polydextrose or modified starch, and salt also can be included.

Confectionery products can be readily prepared by replacing at least a portion of the cocoa butter component of a standard formulation with an oil of the invention using standard methods. See, for example, Minifie, B. W., *Chocolate, Cocoa and Confectionery*, 3rd Ed., Van Nostrand Reinhold, New York, 1989, pp 1–33; and Lees, R., *A Course in Confectionery*, 2nd Ed., Specialised Publications Ltd., Surrey, United Kingdom, 1980, pp. 98–106.

Oils of the invention also can be used to formulate solid fats, such as spreads and shortenings to obtain desired solid fat contents of the products. Margarines contain at least 80% fat, and typically are prepared from hydrogenated oil base stocks. Low trans margarines that currently are available typically contain an oil with a high percentage of polyunsaturated fatty acids blended with hydrogenated palm and babasso oils that have been interesterified. Other low trans margarines contain interesterified liquid oils that are high in linoleic acid content. Oils of the invention can be used as the basis for a stick margarine containing at least about 80% fat or a soft tub spread, which contains less than about 80% fat. A target SFI of a hard stick margarine is, for example, 22–28 at 10° C., 16 at 21.1° C., and 2% at 33.3° C. A target SFI for a soft spread is, for example, 11 at 10° C., 7 at 21.1° C., and 2 at 33.3° C. Margarine or a spread formulated with an oil of the invention also can include water, thickening agents such as gelatin, pectin, carrageenans, agar, or starch, milk products such as spray-dried whey, preservatives such as salt, sodium benzoate, potassium sorbate, and lactic acid, flavor agents, emulsifiers, vitamins, or coloring agents.

Shortenings with the desired solid fat content also can be produced with oils of the invention. All-purpose shortening can have a solid fat content as high as about 35%, with an average solid fat content of about 25% at 10° C. Emulsifiers, antifoam agents such as dimethylpolysiloxane, antioxidants such as tert-butylhydroquinone, butylated hydroxytoluene, and butylated hydroxyanisole, metal chelators such as citric acid, colorants such as carotenes, bixin, and apo-6-carotenal, and flavor agents such as diacetyl also can be added to shortening formulated with an oil of the invention.

The invention will be further described in the following examples, which do not limit the scope of the invention described in the claims.

EXAMPLES

Example 1

Creation of Plant Line C1C Having Elevated Stearic Acid and Reduced Polyunsaturates This example describes the creation of a *Brassica napus* plant line that yields seeds having an increased stearic acid content and a decreased polyunsaturate content. The alteration in fatty acid composition results from the introduction of three different transgenes and two chemically-induced mutant genes into a single line. The first transgene contains an oleoyl-ACP thioesterase coding sequence that confers an increased stearic acid content when overexpressed in a transgenic plant. The second transgene contains a delta-9 fatty acid desaturase coding sequence that inhibits delta-9 desaturase activity by cosuppression. The third transgene contains a delta-12 fatty acid desaturase coding sequence that inhibits delta-12 desaturase activity by antisense. One of the mutations in the plant line is in a fad2 gene, which encodes a delta-12 fatty acid desaturase. The second mutation presumably resides in a fad3 gene, which encodes a delta-15 fatty acid desaturase. These mutations reduce or eliminate delta-12 and delta-15 desaturase activity in *B. napus* and were obtained from *B. napus* line IMC 130. U.S. Pat. No. 5,767,338.

A nucleic acid construct was prepared comprising a soybean acyl-ACP thioesterase coding sequence, as described in U.S. Pat. No. 5,530,186, linked to a phaseolin promoter and a phaseolin polyA terminator sequence. The construct was introduced into a *Brassica napus* canola-type (low erucic acid) variety by Agrobacterium-mediated transformation, using a binary vector system. The thioesterase gene was shown to be stably inherited by molecular analysis and thioesterase activity was shown to be present, based on the increase in stearic acid and palmitic acid in seed oil of transformed plants. After selfing to obtain homozygotes, the line was designated 140-241.

In a second transformation, a soybean delta-9 fatty acid desaturase gene, driven by a napin promoter and linked to a napin polyA terminator element, was introduced into a canola-type *Brassica napus* variety by Agrobacterium-mediated transformation as described above. Transgenic plants were identified in which the delta-9 desaturase gene was stably inherited by molecular analysis and in which desaturase activity was inhibited, based on the increase in stearic acid in seed oil of transformants. After selfing to obtain homozygotes, the cosuppression delta-9 desaturase line was designated 188-173.

A cross of 140-241 X 188-173 was carried out and progeny containing both transgenes in homozygous condition were identified by the elevated stearic acid content in seeds. Seed oil of the double homozygotes contained approximately 7% palmitic acid, 25% stearic acid, 35% oleic acid, 8% α-linolenic acid and 3% arachidonic acid. The line possessing both transgenes in homozygous condition selected for further breeding was designated 241-173.

A third transformation was carried out in which a full-length coding sequence of a *B. napus* delta-12 fatty acid desaturase gene (D gene, WO 98/56239) was linked in antisense orientation to a napin promoter and a napin polyA terminator element. The antisense nucleic acid construct was introduced into a canola-type *Brassica napus* variety by Agrobacterium-mediated transformation as described above. Transgenic plants in which the delta-12 desaturase gene was stably inherited were identified by molecular analysis and in which desaturase activity was inhibited, based on the decrease in linoleic acid in seed oil of transformants. After selfing to obtain homozygotes, one antisense delta-12 desaturase line was designated 158-8. A cross of 158-8 X IMC 130 was carried out and selfed progeny possessing the delta-12 desaturase antisense construct and the IMC 130 mutations were identified by the lower linoleic and α-linolenic acid content in seeds. One line, designated 158-8-IMC130, was selected for further breeding.

A cross of 241-173 X 158-8-IMC130 was carried out. Progeny were identified that contained all three transgenes and both the fad2 and presumptive fad3 mutations in homozygous condition. One line, designated C1C, was selected for further analysis and breeding. The fatty acid composition of C1C seed oil in $F_5$ progeny is shown in Table 1.

TABLE 1

Fatty Acid Composition of C1C Plants

| Plant[1] | 16:0[2] | 18:0 | 18:1 | 18:2 | 18:3 | 20:0 | 20:1 | 22:0 | 22:1 | 24:0 | 24:1 | Sats |
|---|---|---|---|---|---|---|---|---|---|---|---|---|
| 2433-01 | 8.4 | 25.5 | 47.4 | 7.7 | 5.2 | 3.6 | 0.5 | 0.9 | 0.0 | 0.3 | 0.2 | 38.7 |
| 2433-02 | 8.8 | 24.3 | 47.7 | 8.8 | 4.6 | 3.4 | 0.5 | 0.9 | 0.0 | 0.3 | 0.2 | 37.9 |
| 2433-03 | 8.4 | 25.7 | 46.6 | 8.5 | 4.8 | 3.7 | 0.5 | 1.0 | 0.0 | 0.3 | 0.2 | 39.1 |
| 2433-06 | 9.3 | 27.7 | 44.5 | 8.4 | 4.4 | 3.5 | 0.4 | 0.8 | 0.0 | 0.3 | 0.2 | 41.8 |
| 2433-07 | 8.5 | 26.5 | 46.8 | 7.9 | 4.0 | 3.8 | 0.4 | 1.0 | 0.0 | 0.3 | 0.3 | 40.2 |
| 2433-10 | 8.9 | 26.7 | 46.4 | 8.3 | 3.8 | 3.7 | 0.4 | 0.9 | 0.0 | 0.3 | 0.2 | 40.6 |
| 2433-13 | 9.0 | 26.2 | 46.3 | 8.0 | 4.0 | 3.8 | 0.4 | 1.0 | 0.2 | 0.3 | 0.4 | 40.4 |
| 2433-23 | 7.6 | 26.9 | 45.7 | 8.1 | 5.6 | 3.9 | 0.5 | 1.1 | 0.0 | 0.2 | 0.2 | 39.7 |
| 2433-26 | 8.1 | 26.8 | 45.9 | 7.8 | 5.3 | 3.8 | 0.5 | 1.0 | 0.0 | 0.3 | 0.2 | 40.0 |
| 2433-28 | 7.7 | 24.7 | 48.5 | 7.7 | 5.3 | 3.7 | 0.5 | 1.0 | 0.0 | 0.3 | 0.2 | 37.5 |

[1] Bulk seed samples from ten individual $F_5$ C1C plants.
[2] 16:0 = palmitic acid; 18:0 = stearic acid; 18:1 = oleic acid; 18:2 = linoleic acid; 18:3 = α-linolenic acid; 20:0 = arachidonic acid; 20:1 = eicosenoic acid; 22:0 = behenic acid; 22:1 = erucic acid; 24:0 = lignoceratic acid; 24:1 = nervonic acid.

Example 2

Creation of Plant Line LHS015-08 Having Elevated Stearic Acid and Reduced Polyunsaturates This example describes the creation of a *Brassica napus* plant line that yields seeds having an increased stearic acid content and a decreased polyunsaturate content. The 241-173 X 158-8-IMC130 line of Example 1, which carries mutations and transgenes causing overexpression of oleoyl-ACP desaturase and inhibition of delta-9 and delta-12 desaturases, was used in combination with genetic modifications as described below.

A transformation was carried out in which a *B. napus* delta-15 fatty acid desaturase gene, driven by a napin promoter and linked to a napin polyA terminator element, was introduced into a canola-type *Brassica napus* variety by Agrobacterium-mediated transformation as described above. Transgenic plants were identified in which the delta-15 desaturase gene was stably inherited by Southern analysis and in which desaturase activity was suppressed, based on the decrease in α-linolenic acid in seed oil of transformants. After selfing to obtain homozygotes, the cosuppression delta-15 desaturase line was designated 663-40.

A cross of (241-173 X 158-8-IMC130) X 663-40 was carried out. Progeny were identified that contained transgenes and mutations in homozygous condition and yielded seeds having elevated saturates and reduced polyunsaturates. One line was selected and designated LHS015-08. The fatty acid composition of oil extracted from bulk seed samples of LHS015-08 plants at the F4 and F5 generations is shown in Tables 8 and 9.

As shown in Examples 1 and 2, inhibition or reduction in delta-12 and/or delta-15 desaturase activity can be achieved via mutagenesis or through the use of a transgene, e.g., by antisense, ribozyme or cosuppression. It is contemplated that reduction or complete inhibition of delta-9 desaturase activity can be achieved through mutagenesis, e.g., chemical or physical mutagenesis of seeds, followed by selection of the desired mutation event. Alternatively, it is contemplated that reduction or complete inhibition of delta-9 desaturase activity can be achieved through the use of antisense or ribozyme transgenes.

Example 3

Extraction and Analysis of C1C Oil

To extract oil, seeds produced by the plants of the invention were cooked and screw pressed. The cakes that are expelled from the screw press then were solvent extracted using a 4" heat traced column.

The following cooking procedure was employed to extract oil from seeds of the C1C line of Example 1. Seeds of the C1C line were placed in a large steel can containing steam coils (the inner diameter of the can was approximately 12"), and steam was passed through the coils to raise the temperature of the seed. The seeds were cooked at 70° C. for 30 minutes and then broken open with a screw press. While the majority of the oil within the seeds was released by passing them through a screw press, the pressed, seed cake contains some residual oil. The initial seed moisture for the C1C variety was 4.5 wt %, and the final seed moisture was 2.7 wt % (no water was added prior to cooking).

The cakes expelled from the screw press were solvent extracted in batches with hexane. The extraction was carried out in a large steel can (having an inner diameter of approximately 10") by adding 500 grams of pressed seed to 1.5 liters of hexane and heating the mixture over a steam bath to 60° C. while vigorously stirring for 15 minutes. The hexane and oil micella was filtered off and the hexane was evaporated. The cakes were then mixed with fresh hexane, and the process was repeated until insignificant amounts of oil were obtained (<10 grams). The solvent was evaporated from the micella, producing the crude oil.

The crude oil was degummed by adding 0.15% (w/w) of concentrated phosphoric acid to the oil. The oil-acid mixture was heated to 60° C. and stirred rapidly with a mechanical stirrer for 30 minutes. Water was then added (1% w/w) and the mixture was stirred for another 30 minutes. The gum was separated from the oil by centrifuging at 5000 rpm for 15 minutes.

The free fatty acid content of the degummed oil was determined by titration. Isopropanol (20 mls) was placed in an Erlenmeyer flask, and 2–3 drops of a 1% phenolphthalein/isopropanol solution was added. A 0.1 N solution of sodium hydroxide in methanol was added dropwise with stirring until the solution turned pink. At that point, 10 grams of crude oil was added, and the pink color disappeared. The mixture containing the crude oil was then titrated with the base (0.1 N sodium hydroxide) until the pink color reappeared and remained for 30 seconds. The percentage of free fatty acids (FFAs) was then calculated using the following formula:

%FFA=(mls titrant)(normality of base)(28.2)÷grams of crude oil

The oil was refined by heating to 60° C. and adding enough of an 8% sodium hydroxide solution to titrate all of the fatty acids, plus an excess of 25%. The sodium hydroxide solution was added over a period of 5 minutes while rapidly mixing the oil with a mechanical stirrer. After the solution was added, the mixture was stirred for an additional 30 minutes. The soaps were separated from the oil by centrifuging at 5000 rpm for 15 minutes.

The degummed oil was bleached in the following manner. Approximately 0.15% Trisyl was added to the oil and stirred under vacuum for 30 minutes at 60° C. The Trisyl was filtered off and the oil was heated to 90° C. under vacuum. A bleaching clay (1.5% Clairion) was added, and the oil was magnetically stirred for 30 minutes. The spent clay was removed by vacuum filtration and the filtered oil was transferred to a glass container, flushed with argon, and allowed to cool. As there was not enough oil for deodorization, the bleached oil was placed under vacuum, in a Parr reactor, and heated to 500° F. (260° C.) for approximately 30 minutes.

The C1C seeds and oils were weighed throughout the process of extraction and refinement. The results are as follows:

| | |
|---|---|
| Seed weight | 850 grams; |
| After cooking and expelling oil | 741 grams; |
| Actual Oil Recovered (oil was not completely free of hexane) | 313 grams; |
| FFA, Chlorophyll measurements | 4.09 grams; |
| Oil Remaining | 309 grams; |
| Gums | 0.87 grams; |
| Soap | 2.47 grams; |
| Oil used for FFA measurements | 2.01 grams; |
| Oil remaining | 276 grams; |
| Oil after Trisyl and Bleach | 260 grams; |
| After Deodorization** | 252 grams |

**heated under vacuum.

The characteristics of the processed C1C oil, including the color and percentage of free fatty acids are shown in Table 2. Crude chlorophyll content was measured according to AOCS Official Method Cc Bd-55. Lovibond color, an indication of the red (carotenoids) and yellow (chlorophyll) color components of an oil was measured according to AOCS Official Method Cc Be-92 using a McCloskey colorimeter (McCloskey Scientific Industries).

TABLE 2

C1C Oil Characteristics

| Sample | Crude Chlorophyll-a ppm | Crude FFA % | RB Oil Lovibond Yellow/Red | RBD Oil Chlorophyll-a ppm | RB Oil Lovibond Yellow/Red | RBD Oil Chlorophyll-b ppm |
|---|---|---|---|---|---|---|
| C1C oil | 1.5 | 0.212 | 20.1/13.3 | 0 | 2.2/.4 | 0 |

The fatty acid distribution was determined according to AOCS Official Method Ce 1c-89. Iodine values were calculated from the FAD according to AOCS Method Cd 1c-85. As shown in Table 3, C1C oil contained high levels of stearic acid (about 20%).

TABLE 3

Fatty Acid Composition of C1C Oil

| Type | 16.0 | 16:1 | 18:0 | 18:1 | 18:2 | 18:3 | 20:0 | 22:0 | 22:1 | 24:0 | 24:1 | IV |
|---|---|---|---|---|---|---|---|---|---|---|---|---|
| C1C Oil | 7.79 | 0.4 | 19.75 | 54.29 | 7.88 | 4.78 | 3.06 | 0.85 | — | 0.27 | 0.15 | 73.56 |

The C1C oil was characterized further by measuring the refractive index (RI), melting point, tocopherol content, oxidative stability, metal, sulfur content, peroxide value, and Mettler Drop Point.

RI was measured at 21° C. with an ABBE Mark II refractometer (Reichert Scientific Instruments, Buffalo, N.Y.). Melting point was measured with DSC on a Perkin Elmer Model 7 differential scanning colorimeter. Samples of 7–12 mg were placed in the sample pans, sealed and loaded into the autosampler. The samples were cooled from an initial temperature of 50° C. to a final temperature of −30° C. at a rate of 5° C. per minute. After equilibrating at −30° C. for 15 minutes, a final DSC scan was recorded from −30° C. to 50° C. at a rate of 5° C. per minute. Melting point of the samples was taken from the DSC profile at the point where 98% of the material was melted.

Tocopherol content was measured according to AOCS Official Method Ce 7-87. Phosphorus content was measured by AOCS Official Method Ca 12-55(93). Oxidative stability was measured using an Oxidative Stability Index instrument, Omnion, Inc., Rockland, Mass., according to AOCS Official Method Cd 12b-92 (revised 1993). This method is an automated replacement for the Active Oxygen Method (AOM) procedure, AOCS Official Method Cd 12-57. Stability was reported in AOM hours.

Metal content was measured according to AOCS Official Method Ca 18-79 using atomic absorption spectrometry with a graphite furnace. Copper and iron are reported in parts per million (ppm). Sulfur was detected by AOCS Official Method Ca 8a-35 (90).

Peroxide value (PV) was measured according to AOCS Official Method Cd 8-53 using isooctane in place of chloroform. PV measures the extent of primary oil oxidation. Mettler Drop Point, the minimum temperature at which an oil flows through a defined orifice, was measured according to AOCS Official Method Cc 18-80.

As shown in Table 4, the level of phosphorous in C1C oil was elevated, suggesting that the bleaching process described above was sub-optimal. Ideally, phosphorous levels should be <3 ppm. The bleaching process can be altered readily to adjust the phosphorous level.

TABLE 4

Processed Oil Analysis

| Type | RI | Melting Point (DSC) | Tocopherol ppm | AOM Hours | Cu ppm | Fe ppm | Phosphorous ppm | Sulfur ppm | Peroxide Value meq/kg | Mettler Drop Pt |
|---|---|---|---|---|---|---|---|---|---|---|
| C1C oil | 1.47 | 5.3, 24* | 600 | 27.99 | <.05 | 0.33 | 6.84 | <.50 | 2.45 | 20.5° C. |

*Following a cold storage period

Example 4

Alteration of Melting Point

The melting temperatures and melting profiles of the oils of the invention are of particular interest. After refining and bleaching of endogenous oil, C1C oil had a melting point of 9.96° C. However, after the oil was incubated at 6° C. for two months, the DSC profile revealed a shift in the melting point to 27° C. This suggests that the oil was converted to a crystal (polymorphic) form that had a higher melting point.

Additional experiments were performed to examine the changes in the melting point, which occurred when the oil was stored at cold temperatures. C1C oil (stored at 6° C. for two months) was taken out of cold storage and quickly loaded into the DSC. Extra care was taken to prevent the material from melting during the DSC preparation. The sample was cooled to 0° C. and then brought to 60° C. at a rate of 5° C./minute. As shown in FIG. 1, line 1, the material melted between 25° C. and 28° C. By the time the sample reached 60° C., the structural memory was completely erased. At this point, the oil was cooled to −30° C. and again heated to 60° C. Upon heating for the second time, the majority of the oil melted between −20° C. and 5° C. This indicates that the oil was no longer in the higher melting crystal form. The oil was cooled to 0° C. again, then warmed to 10° C. and held for 1 hour. The oil was then cooled to 0° C. and heated again to 60° C. The DSC profile indicated that holding the oil at 10° C. for an hour did not allow the oil to crystallize into the form with the higher melting temperature (FIG. 1, line 3). The procedure was repeated, except the oil was incubated at 10° C. for 15 hours. When the DSC profile was taken again, the melting temperature and enthalpy of melting were significantly higher as the oil melted between 10° C. and 25° C. (FIG. 1, line 2).

A fractionation scheme was devised based on the results of the DSC studies. A sealed jar containing 73.75 grams of C1C oil was incubated in a circulating water bath (Fisher Isotemp, Model 910) for 15 hours at 10° C. The temperature was raised to 16° C. and the incubation was continued for an additional 24 hours. The oil was fractionated by centrifugation (10,000 rpm for 20 minutes at 16° C.) to produce about 41.37 grams of stearine #1 (56% yield) and about 23.26 grams of olein #1 (31.5% yield).

Figure 2:
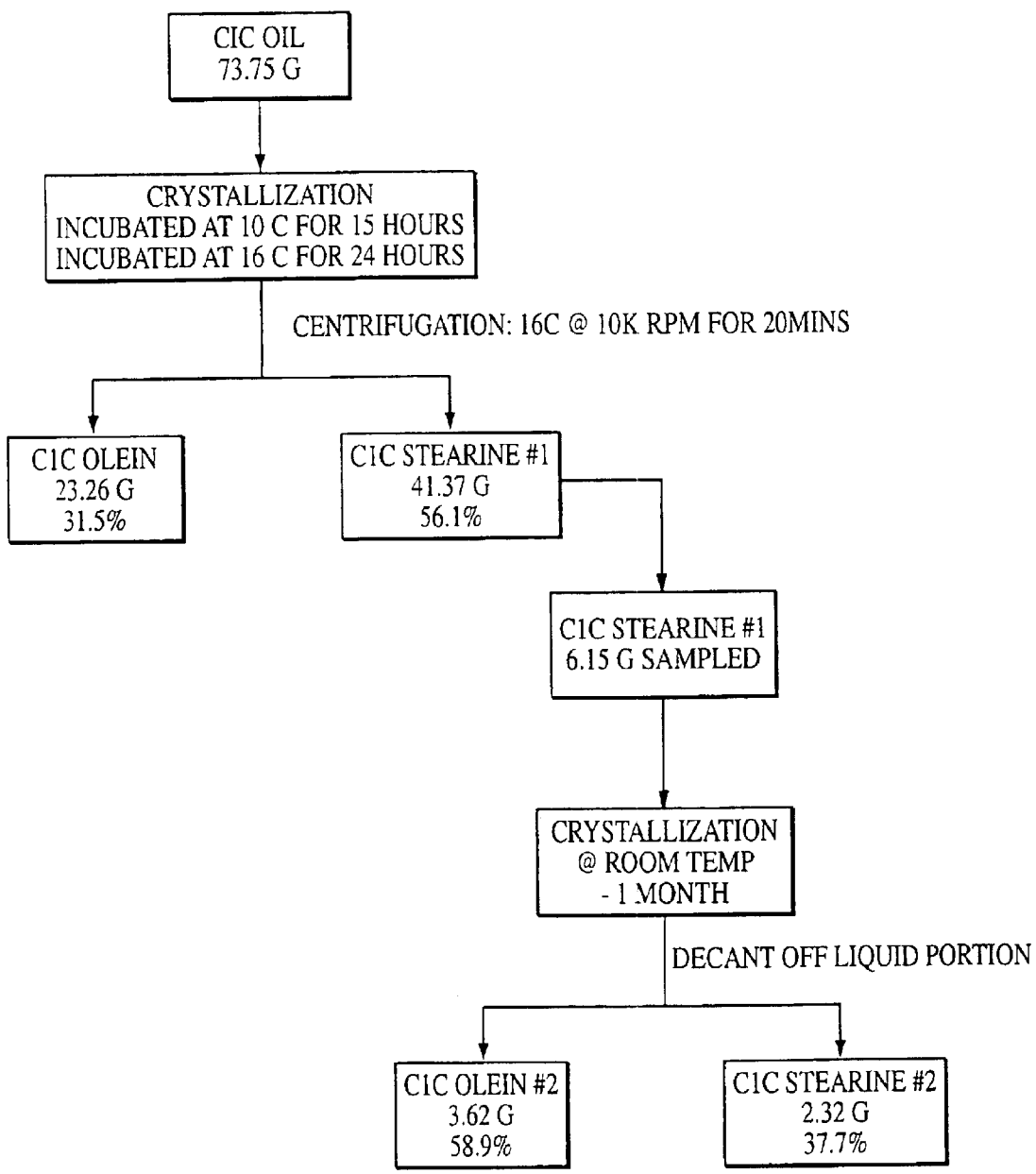
FIG. 2 shows a scheme for fractionating C1C oil.

After stearine #1 was melted and allowed to sit at room temperature (approximately 20° C.), the oil slowly underwent a second crystallization. Over a period of one month, the crystallization produced small spherical particles (1–2 mm in diameter), and did not appear to entrap much olein. The distinct solid and liquid phases were easily separated by decanting into olein #2 and stearine #2 fractions. The fractionation scheme is shown in FIG. 2. The fatty acid compositions of the parent oil and the stearine and olein fractions are shown in Table 5.

TABLE 5

Fatty Acid Composition of C1C Oil Fractions

| Type | 16:0 | 16:1 | 18:0 | 18:1 | 18:2 | 18:3 | 20:0 | 22:0 | 22:1 | 24:0 | 24:1 | IV | MP |
|---|---|---|---|---|---|---|---|---|---|---|---|---|---|
| C1C | 7.79 | 0.4 | 19.75 | 54.29 | 7.88 | 4.78 | 3.06 | 0.85 | — | 0.27 | 0.15 | 73.56 | 28 |
| Stearine #1 | 7.92 | 0.33 | 22.01 | 52.31 | 7.36 | 4.36 | 3.38 | 0.9 | 0.01 | 0.29 | 0.13 | 69.77 | 29.65 |
| Olein #1 | 7.33 | 0.41 | 16.27 | 57.42 | 8.43 | 5.08 | 2.72 | 0.75 | 0.01 | 0.26 | 0.14 | 78.09 | 3.38 |
| Stearine #2 | 7.84 | 0.3 | 26.39 | 48.84 | 6.5 | 3.84 | 3.91 | 1.01 | 0.01 | 0.3 | 0.11 | 63.9 | 36.9 |
| Olein #2 | 8.02 | 0.4 | 17.97 | 55.1 | 8.2 | 4.86 | 3.01 | 0.84 | 0.01 | 0.27 | 0.14 | 75.19 | 4.59 |

The largest difference in fatty acid composition between stearine #2 and olein #2 is seen with the C18:0 and C18:1 fatty acid content. The olein fraction contains 6% less C18:0 and 5% more C18:1. However, the melting temperature between the two fractions was very different. The stearine fraction has a melting point of about 27.7° C., whereas the olein fraction has a melting point of about 3° C. The large difference in melting temperature is consistent with a mechanism in which TAG structure plays a significant role in determining the melting temperature and solid fat content.

TAG analysis was performed on the C1C oil and four subfractions (olein #1, stearine #1, olein #2, and stearine #2). The results are shown in Table 6 (ND=not determined in Table 6). Linolenic acid and linoleic acid are abbreviated as "Ln" and "L", respectively. As shown in Table 6, POP, POS, and SOS compose about 19% of the TAGs of the stearine #1 fraction. In the stearine #2 fraction, POP, POS and SOS compose about 31% of the TAGs. The solid fat content for C1C and the C1C stearine fractions is shown in Table 7.

TABLE 6

TAG Analysis of C1C and Subfractions

| TAG | C1C | C1C Olein #1 | C1C Stearine #1 | C1C Olein #2 | C1C Stearine #2 |
|---|---|---|---|---|---|
| LnOO | 2.72 | 2.96 | 2.3 | 3.43 | 2.21 |
| LLP | 1.76 | 1.93 | 1.7 | 1.94 | ND |
| LnOP | 0.86 | ND | ND | 2.46 | ND |
| LOO | 4.52 | 4.91 | 4.17 | 6.86 | 3.81 |
| LOP | 6.43 | 7.44 | 5.79 | 9.79 | 5.19 |
| PLP | 1.54 | 1.38 | 1.41 | 2.04 | 2.13 |
| OOO | 14.67 | 15.27 | 13.1 | 20.06 | 11.83 |
| LOS | 6.33 | 8.29 | 6.29 | 9.85 | 5.0 |
| POO | 12.54 | 10.75 | 9.43 | 15.25 | 8.25 |
| POP | 1.55 | 1.38 | 2.11 | 2.3 | 2.4 |
| PLS | 1.25 | 1.17 | ND | ND | ND |
| SLnS | 1.14 | ND | 1.12 | ND | ND |
| OOS | 24.68 | 29.97 | 23.33 | 9.57 | 26.32 |
| SLS | 1.02 | ND | ND | 6.03 | 3.17 |
| POS | 4.41 | 2.83 | 6.11 | 6.06 | 7.88 |
| OOA | 3.44 | 3.81 | 3.32 | 6.01 | 2.1 |
| SPP | 0.9 | ND | ND | 2.0 | ND |
| SOS | 6.77 | 2.06 | 10.75 | 6.16 | 20.9 |
| SSS | 0.93 | trace | trace | trace | trace |

TABLE 7

Solid Fat Content for C1C and Stearine Fractions

| Temp ° C. | C1C | C1C Stearine #1 | C1C Stearine #2 |
|---|---|---|---|
| 10 | 16.6% | 24.5% | 42.8% |
| 21.1 | 0.1% | 0.8% | 20.5% |
| 26.7 | 0% | 0% | 13.9% |
| 33.3 | 0% | 0% | 0.8% |
| 40 | 0% | 0% | 0% |

Example 5

High Stearic Oil

Oil was extracted from bulk seed samples from the LHS015-08 plants of Example 2. Fatty acid compositions are shown in Tables 8 and 9.

TABLE 8

Fatty Acid Composition in Seeds of an $F_4$ LHS015-08 Plant

| 16:0 | 18:0 | 18:1 | 18:2 | 18:3 | 20:0 | 20:1 | 22:0 | 22:1 | 24:0 | 24:1 | Sats |
|---|---|---|---|---|---|---|---|---|---|---|---|
| 7.8 | 24.8 | 53.8 | 4.8 | 1.4 | 4.6 | 0.5 | 1.3 | 0.0 | 0.4 | 0.2 | >38.5 |

TABLE 9

Fatty Acid Composition of LHS015-08 Seeds[1]

| Fatty Acid | Plot 1 | Plot 2 | AVE |
|---|---|---|---|
| C16:0 | 7.5 | 7.4 | 7.4 |
| C16:1 | 0.4 | 0.4 | 0.4 |
| C18:0 | 17.6 | 19.2 | 18.4 |
| C18:1 | 63.8 | 62.1 | 62.9 |
| C18:2 | 4.3 | 4.3 | 4.3 |
| C18:3 | 1.1 | 1.1 | 1.1 |
| C20:0 | 3.0 | 3.1 | 3.1 |
| C20:1 | 0.6 | 0.6 | 0.6 |
| C20:2 | 0.0 | 0.0 | 0.0 |
| C22:0 | 0.9 | 0.9 | 0.9 |
| C22:1 | 0.0 | 0.0 | 0.0 |
| C24:0 | 0.2 | 0.2 | 0.2 |
| C24:1 | 0.4 | 0.6 | 0.5 |
| Sats | >28.9 | >30.6 | >29.8 |

[1]Bulk seed samples pooled from each of two different plots of $F_5$ plants.

Seeds from plot 1 and 2 (Table 9) were pooled, and oil was extracted. Table 10 provides the fatty acid composition of the oil (LHS015-08) extracted from the pooled seeds. The level of polyunsaturated fatty acids in this oil (5.10%) was lower than the polyunsaturated content of the C1C oil (Table 3, 12.66%). Tocopherol and oxidative stability tests indicated that this oil also had less tocopherol than the C1C oil and had higher oxidative stability (Table 11). The increase in oxidative stability is thought to be due to the reduction in polyunsaturated fatty acids.

TABLE 10

Fatty Acid Composition of $F_5$ LHS015-08 Oil

| 16:0 | 18:0 | 18:1 | 18:2 | 18:3 | IV | Sats | Monos | Polys |
|---|---|---|---|---|---|---|---|---|
| 4.78 | 18.12 | 63.21 | 4.08 | 0.99 | 64.82 | 30.33 | 64.32 | 5.10 |

TABLE 11

Tocopherol Content and Oxidative Stability of High Stearic Oils

| Oil | Tocopherol (ppm) | AOM #1 | AOM #2 | Ave AOM |
|---|---|---|---|---|
| C1C | 600 | 23 | — | 23 |
| LHS015-08 | 420 | 106 | 102 | 104 |

The addition of 200 ppm of the antioxidant TBHQ resulted in an approximately 70% increase in oxidative stability (Table 12).

TABLE 12

Oxidative Stability of High Stearic Oils with TBHQ

| Oil | AOM #1 | AOM #2 | Ave AOM |
|---|---|---|---|
| LHS015-8 + TBHQ | 172 | 171 | 171.5 |

The $F_5$ LHS015-08 oil was crystallized and fractionated into stearine and olein portions. Approximately 329 g of the oil was poured into a centrifuge container and placed in a refrigerator over night (5° C.). The container then was transferred to a water bath (7° C.) and kept for 24 hours. The temperature of the water bath was raised to 15° C. and left for 24 hours, then centrifuged at 8000 rpm for 20 minutes, in a precooled centrifuge kept at 15° C. The fractions were separated by suction, yielding 221.54 grams of stearine (67% yield) and 107.68 grams of olein (33% yield). The fatty acid content of the unfractionated oil, and the stearine and olein fractions are shown in Table 13.

TABLE 13

Fatty Acid Composition of $F_5$ LHS015-08 Oil and Stearine and Olein Fractions

| Oil | 16:0 | 18:0 | 18:1 | 18:2 | 18:3 | IV | Sats | Monos | Polys |
|---|---|---|---|---|---|---|---|---|---|
| Unfractionated | 4.78 | 18.12 | 63.21 | 4.08 | 0.99 | 64.82 | 30.33 | 64.32 | 5.10 |
| Stearine | 7.76 | 19.83 | 61.24 | 3.91 | 0.97 | 62.73 | 32.57 | 62.28 | 4.89 |
| Olein | 7.07 | 14.31 | 67.38 | 4.56 | 1.15 | 69.81 | 25.36 | 68.61 | 5.77 |

DSC was performed with the unfractionated $F_5$ LHS015-08 oil and the stearine and olein fractions, as described in Example 4. The results are shown in Table 14. The sample labeled "after incubation" was heated from 20° C. to 75° C. at a rate of 40° C. per minute and held at 75° C. for 10 minutes, then cooled to −20° C. at a rate of 5° C. per minute and held at −20° C. for 30 minutes. The sample then was heated to 7° C. at a rate of 1° C. per minute and held at 7° C. for 12 hours. After this incubation, the sample was cooled to −10° C. at a rate of 1° C. per minute and held at −10° C. for 10 minutes, then finally heated to 75° C. at a rate of 1° C. per minute. $F_5$ LHS015-08 oil had a melting point of 15.5° C. and began to crystallize at 3° C., while the sample that was incubated had a higher melting point (25° C.). The stearine fraction of $F_5$ LHS015-08 had a melting point of 29.3° C. and began to crystallize at 5.7° C.

TABLE 14

DSC Data

| Oil | Melting Point ° C. | Onset of Crystallization ° C. | ΔH (j/g) |
|---|---|---|---|
| $F_5$ LHS015-08 | 15.5 | 3.0 | 70.9 |
| $F_5$ LHS015-08 after incubation | 24.61 | 2.9 | 71.1 |
| Stearine Fraction | 29.3 | 5.7 | 72.7 |
| Olein Fraction | 7.5 | −2.0 | 66.7 |

The TAG profiles of $F_5$ LHS015-08 oil (unfractionated) and the olein and stearine fractions were analysed by HPLC, as described in Example 4, and are indicated in Table 15. Linolenic acid, linoleic acid, arachidonic acid (C20:0), and behenic acid (C22:0) are abbreviated as "Ln", "L", "A", and "B", respectively. The TAG analysis indicated that SOS and POS are concentrated in the stearine portion during fractionation. As shown in Table 15, POP, POS, and SOS compose about 15.5% of the TAGs in the stearine fraction.

TABLE 15

TAG Profile of $F_5$ LHS015-08 (HPLC)

| TAG | Unfractionated | Stearine | Olein |
|---|---|---|---|
| OLnO | 0.21 | 0.25 | 0.27 |
| OLO | 1.53 | 1.43 | 1.85 |
| PLO | 1.08 | 0.93 | 1.17 |
| OOO | 26.63 | 25.27 | 30.11 |
| SLO | 2.92 | 2.74 | 2.85 |
| POO | 12.98 | 12.00 | 14.56 |
| POP | 1.02 | 1.00 | 0.80 |
| SOO | 38.42 | 36.03 | 41.43 |
| POS | 3.23 | 4.36 | 1.17 |
| OOA | 3.42 | 3.13 | 3.60 |
| SOS | 6.34 | 10.09 | 0.97 |
| OOB | 0.57 | 0.49 | 0.53 |
| SOA | 0.87 | 1.41 | 0.15 |
| SOB | 0.17 | 0.33 | 0.03 |

The solid fat content of the $F_5$ LHS015-08 oil and its stearine fraction, as well as the stearine fraction with 2% added soy stearine was determined (Table 16). The solid fat content of soft/tub and stick margarine are provided as reference values. After the tempering period described for the DSC profile, LHS015-08 oil was solid at room temperature. This improved solid fat behavior is thought to be due to an increase in TAGs such as SOS and POS, which contribute to the high temperature melting crystal net work. As indicated in Table 16, the solid fat content of the stearine fraction of $F_5$ LHS015-08 was higher than that of the unfractionated oil and was comparable to that of stick margarine. Addition of 2% soy stearine further increased the solid fat content.

TABLE 16

Solid Fat Content of LHS015-08 Oil and Its Fractions

| Sample | 10.0° C. | 21.1° C. | 26.7° C. | 33.3° C. | 37.8° C. | 40.0° C. |
|---|---|---|---|---|---|---|
| LHS015-08 | 12.48 | 0 | 0 | 0 | 0 | 0 |
| Stearine | 21.42 | 0.88 | 0 | 0 | 0 | 0 |
| Stearine + 2% Soy Stearine | 25.16 | 7.24 | 3.93 | 2.09 | 0.98 | 1.17 |
| Soft/tub Margarine | 8–12 | 4–7 | | 1–3 | | |
| Stick Margarine | 22–25 | 13–16 | | 2–4 | | |

Other Embodiments

It is to be understood that while the invention has been described in conjunction with the detailed description thereof, the foregoing description is intended to illustrate and not limit the scope of the invention, which is defined by the scope of the appended claims.

What is claimed is:

1. An endogenous oil extracted from plant seeds, said oil having a stearic acid content of about 15% to about 30%, an oleic acid content of about 34% to about 53%, and a polyunsaturated fatty acid content of about 2% to about 6%.

2. The oil of claim 1, wherein said stearic acid content is about 17% to about 28%.

3. The oil of claim 1, wherein said oil has an α-linolenic acid content of about 0.6% to about 2.0%.

4. The oil of claim 1, said oil further having a palmitic acid content of about 6% to about 20%.

5. The oil of claim 4, wherein said palmitic acid content is about 7% to about 19%.

6. The oil of claim 1, wherein said oil has an iodine value of less than about 76.

7. The oil of claim 1, wherein said oleic acid content is about 46% to about 53%.

8. The oil of claim 1, wherein said oil has a DSC melting point of about 4° C. to about 20° C. in the absence of cold storage crystallization and a DSC melting point of about 24° C. to about 40° C. following cold storage crystallization.

9. The oil of claim 1, said oil having a stearic acid content of about 19% to about 30%.

10. The oil of claim 9, said oil further having a palmitic acid content of about 6% to about 19%.

11. The oil of claim 9, said oil further having an oleic acid content of about 46% to about 53%.

12. The oil of claim 9, wherein said oil has a DSC melting point of about 30° C. to about 40° C. in the absence of a cold storage period.

13. The oil of claim 9, wherein about 15% or more of the triacylglycerols in said oil comprise an oleate moiety at the sn-2 position and palmitate or stearate moieties at the sn-1 and sn-3 positions.

14. The oil of claim 13, wherein about 30% or more of the triacylglycerols in said oil comprise an oleate moiety at the sn-2 position and palmitate or stearate moieties at the sn-1 and sn-3 positions.

15. The oil of claim 9 wherein about 18% or more of the triacylglycerols in said oil comprise an oleate moiety at the sn-2 position and palmitate or stearate moieties at the sn-1 and sn-3 positions.

16. The oil of claim 9, wherein about 10% to about 25% of the triacylglycerols in said oil have a stearate moiety at the sn-1 position, an oleate moiety at the sn-2 position, and a stearate moiety at the sn-3 position; and about 6% to about 12% of triacylglycerols in said oil have a palmitate moiety at the sn-1 position, an oleate moiety at the sn-2 position, and a stearate moiety at the sn-3 position.

17. The oil of claim 1, wherein said oil is extracted from Brassica seeds.

18. A vegetable oil, wherein at least about 15% of the triacylglycerols in said oil comprise an oleate moiety at the sn-2 position and palmitate or stearate moieties at the sn-1 and sn-3 positions, and wherein said vegetable oil is selected from the group consisting of corn, sunflower, soybean, and canola oil.

19. The vegetable oil of claim 18, wherein at least about 18% of the triacylglycerols in said oil comprise an oleate moiety at the sn-2 position and palmitate or stearate moieties at the sn-1 and sn-3 positions.

20. The vegetable oil of claim 18, wherein at least about 30% of the triacylglycerols in said oil comprise an oleate moiety at the sn-2 position and palmitate or stearate moieties at the sn-1 and sn-3 positions.

21. A method of producing a vegetable oil, comprising:
   a) crushing seeds produced by a plant, said seeds having a stearic acid content of about 15% to about 30%, an oleic acid content of about 34% to about 53%, and a polyunsaturated fatty acid content of about 2% to about 6%; and
   b) extracting an endogenous oil from the crushed seeds.

22. The method of claim 21, wherein said plant is a Brassica plant.

23. The method of claim 22, wherein said Brassica plant exhibits reduced delta-9 desaturase activity and reduced delta-12 desaturase activity, and increased stearoyl acyl-ACP thioesterase activity.

24. The method of claim 23, wherein said Brassica plant further exhibits a reduced delta-15 desaturase activity.

25. The method of claim 21 wherein said endogenous oil has a palmitic acid content of about 6% to about 20%.

26. The method of claim 21, further comprising the step of fractionating said endogenous oil into a stearine fraction and an olein fraction, said stearine fraction having a stearic acid content of about 20% to about 30% and an oleic acid content of about 46% to about 53%.

27. A confectionery product comprising a fat component, said fat component having a stearic acid content of about 20% to about 30%, an oleic acid content of about 34% to about 53%, and a polyunsaturated fatty acid content of about 2% to about 6%.

28. The confectionery product of claim 27, wherein said vegetable oil has an oleic acid content of about 46% to about 53%.

29. A confectionery product comprising a fat component, wherein at least about 18% of the triacylglycerols in said fat component comprise an oleate moiety at the sn-2 position and palmitate or stearate moieties at the sn-1 and sn-3 positions, and wherein said fat component is derived from canola, soy, corn, or sunflower oil.

30. The confectionery product of claim 29 wherein said fat component is derived from canola.

31. The confectionery product of claim 29, wherein said fat component is derived from soy.

32. The confectionery product of claim 29, wherein said fat component is derived from sunflower.

33. The confectionery product of claim 29, wherein said fat component is derived from corn.

34. A vegetable oil having a stearic acid content of about 15% to about 30%, an oleic acid content of about 34% to about 53%, and a polyunsaturated fatty acid content of about 2% to about 15%, wherein said vegetable oil is canola, corn, soy, or sunflower oil.

35. The vegetable oil of claim 34, wherein said vegetable oil is canola oil.

36. The vegetable oil of claim 34, wherein said vegetable oil is corn oil.

37. The vegetable oil of claim 34, wherein said vegetable oil is sunflower oil.

38. The vegetable oil of claim 34 wherein said vegetable oil is soy oil.

39. The vegetable oil of claim 34, wherein said α-linolenic acid content is about 0.6% to about 2%.

40. The vegetable oil of claim 34, wherein said palmitic acid content is about 7% to about 19%.

* * * * *